United States Patent
Kaiser et al.

(10) Patent No.: US 10,864,120 B2
(45) Date of Patent: Dec. 15, 2020

(54) ABSORBENT ARTICLE WITH FLUID CONTROL FEATURES

(71) Applicant: Attends Healthcare Products, Inc., Greenville, NC (US)

(72) Inventors: Thomas A. Kaiser, Marion, OH (US); Trenton T. Ottery, Delaware, OH (US); Steven D. Linton, Snellville, GA (US)

(73) Assignee: ATTENDS HEALTHCARE PRODUCTS, INC., Greenville, NC (US)

( * ) Notice: Subject to any disclaimer, the term of this patent is extended or adjusted under 35 U.S.C. 154(b) by 412 days.

(21) Appl. No.: 14/628,072

(22) Filed: Feb. 20, 2015

(65) Prior Publication Data

US 2015/0238369 A1 Aug. 27, 2015

Related U.S. Application Data

(60) Provisional application No. 62/062,409, filed on Oct. 10, 2014, provisional application No. 61/943,038, filed on Feb. 21, 2014.

(51) Int. Cl.
*A61F 13/53* (2006.01)
*A61F 13/532* (2006.01)
*A61F 13/15* (2006.01)

(52) U.S. Cl.
CPC ........ *A61F 13/53* (2013.01); *A61F 13/15634* (2013.01); *A61F 13/532* (2013.01); *A61F 2013/530379* (2013.01); *Y10T 156/1026* (2015.01)

(58) Field of Classification Search
CPC .... A61F 13/47; A61F 13/472; A61F 13/4751; A61F 13/4756; A61F 13/53; A61F 13/532; A61F 13/533; A61F 2013/530437; A61F 2013/530445
See application file for complete search history.

(56) References Cited

U.S. PATENT DOCUMENTS

| | | | | |
|---|---|---|---|---|
| 2,891,544 A | * | 6/1959 | London | .................. A61F 13/141 2/267 |
| 3,430,629 A | * | 3/1969 | Murphy | ............ A61F 13/49426 604/372 |
| 3,844,288 A | | 10/1974 | Kiela | |

(Continued)

FOREIGN PATENT DOCUMENTS

| EP | 0157649 | 7/1990 |
|---|---|---|
| EP | 0214867 | 6/1991 |

(Continued)

OTHER PUBLICATIONS

Machine translation of JP 2012-187354, Hayashi, Toshihisa, et al., 2012.*
Human Translation of JP 2012-187354, Hayashi et al., Oct. 2012.*

*Primary Examiner* — Kathryn E Ditmer
(74) *Attorney, Agent, or Firm* — Norton Rose Fulbright US LLP

(57) ABSTRACT

Absorbent cores for use in absorbent articles are presented. The absorbent cores include a low-density zone that is surrounded by zones having a higher density than that of the low-density zone. The low-density zone aids in fluid absorption, distribution and storage.

10 Claims, 7 Drawing Sheets

(56) References Cited

U.S. PATENT DOCUMENTS

| | | | | |
|---|---|---|---|---|
| 3,889,679 A * | 6/1975 | Taylor | A61F 13/532 | 604/378 |
| 3,908,659 A * | 9/1975 | Wehrmeyer | A61F 13/533 | 604/374 |
| 3,993,820 A | 11/1976 | Repke | | |
| 4,016,628 A * | 4/1977 | Kolbach | A61F 13/15658 | 19/148 |
| 4,027,672 A * | 6/1977 | Karami | B32B 5/14 | 604/380 |
| 4,074,721 A * | 2/1978 | Smits | A61F 13/141 | 450/37 |
| 4,079,739 A * | 3/1978 | Whitehead | A61F 13/15674 | 604/365 |
| 4,136,699 A | 1/1979 | Collins et al. | | |
| 4,213,459 A * | 7/1980 | Sigl | A61F 13/532 | 604/380 |
| 4,443,512 A * | 4/1984 | Delvaux | A61F 13/533 | 428/162 |
| 4,460,364 A | 7/1984 | Chen et al. | | |
| 4,560,372 A * | 12/1985 | Pieniak | A61F 13/532 | 604/366 |
| 4,685,915 A * | 8/1987 | Hasse | A61F 13/532 | 604/378 |
| 4,701,177 A * | 10/1987 | Ellis | A61F 13/47218 | 604/358 |
| 4,718,152 A * | 1/1988 | Suzuki | D04H 18/04 | 28/104 |
| 4,753,644 A * | 6/1988 | Cottenden | A61F 5/4401 | 604/378 |
| 4,781,710 A * | 11/1988 | Megison | A61F 13/47 | 604/378 |
| 4,834,735 A | 5/1989 | Alemany et al. | | |
| 4,892,536 A | 1/1990 | DesMarais et al. | | |
| 4,895,568 A | 1/1990 | Enloe | | |
| 4,950,264 A * | 8/1990 | Osborn, III | A61F 13/15203 | 604/385.08 |
| 4,988,344 A | 1/1991 | Reising et al. | | |
| 4,988,345 A | 1/1991 | Reising | | |
| 5,009,650 A * | 4/1991 | Bernardin | A61F 13/49009 | 604/368 |
| 5,009,653 A * | 4/1991 | Osborn, III | A61F 13/15203 | 604/378 |
| 5,047,023 A | 9/1991 | Berg | | |
| 5,104,396 A * | 4/1992 | Oatley | A61F 13/532 | 604/379 |
| 5,134,007 A | 7/1992 | Reising et al. | | |
| 5,149,334 A | 9/1992 | Lahrman et al. | | |
| 5,151,091 A * | 9/1992 | Glaug | A61F 13/4756 | 604/378 |
| 5,180,622 A | 1/1993 | Berg et al. | | |
| 5,196,000 A | 3/1993 | Clear et al. | | |
| 5,207,662 A * | 5/1993 | James | A61F 13/15211 | 604/364 |
| 5,281,207 A * | 1/1994 | Chmielewski | A61F 13/535 | 604/368 |
| 5,300,053 A | 4/1994 | Genaro | | |
| 5,324,278 A | 6/1994 | Visscher et al. | | |
| 5,348,547 A | 9/1994 | Payne et al. | | |
| 5,364,382 A | 11/1994 | Latimer et al. | | |
| 5,419,956 A | 5/1995 | Roe | | |
| 5,422,169 A * | 6/1995 | Roe | A61L 15/18 | 428/212 |
| 5,429,629 A | 7/1995 | Latimer et al. | | |
| 5,447,506 A | 9/1995 | Lindquist | | |
| 5,451,442 A * | 9/1995 | Pieniak | A61F 13/4942 | 428/167 |
| H1511 H * | 12/1995 | Chappell | A61F 13/5116 | 604/367 |
| 5,505,718 A | 4/1996 | Roe et al. | | |
| 5,540,796 A | 7/1996 | Fries | | |
| 5,575,785 A * | 11/1996 | Gryskiewicz | A61F 13/49426 | 604/385.28 |
| 5,578,024 A * | 11/1996 | Mizutani | A61F 13/51394 | 604/370 |
| 5,578,025 A * | 11/1996 | May | A61F 13/15203 | 604/368 |
| 5,584,828 A | 12/1996 | Yamamoto et al. | | |
| 5,599,337 A * | 2/1997 | Mccoy | A61F 13/47227 | 604/367 |
| 5,624,423 A * | 4/1997 | Anjur | A61F 13/4757 | 604/369 |
| 5,643,238 A * | 7/1997 | Baker | A61F 13/5323 | 156/276 |
| 5,788,684 A * | 8/1998 | Abuto | A61F 13/532 | 604/358 |
| 5,795,344 A * | 8/1998 | Chappell | A61F 13/533 | 604/379 |
| 5,795,345 A * | 8/1998 | Mizutani | A61F 13/4756 | 604/380 |
| 5,807,365 A | 9/1998 | Luceri | | |
| 5,810,798 A | 9/1998 | Finch et al. | | |
| 5,817,079 A | 10/1998 | Bergquist et al. | | |
| 5,817,271 A * | 10/1998 | Congleton | A61F 13/15707 | 219/121.68 |
| 5,827,387 A | 10/1998 | Reynolds et al. | | |
| 5,846,231 A * | 12/1998 | Fujioka | A61F 13/515 | 604/380 |
| 5,849,002 A | 12/1998 | Carlos et al. | | |
| 5,863,288 A * | 1/1999 | Baker | A61F 13/5323 | 156/276 |
| 5,941,863 A * | 8/1999 | Guidotti | A61F 13/535 | 604/358 |
| 5,947,945 A | 9/1999 | Cree et al. | | |
| 6,068,620 A * | 5/2000 | Chmielewski | A61F 13/15658 | 604/358 |
| 6,099,515 A * | 8/2000 | Sugito | A61F 13/4946 | 604/385.01 |
| 6,160,197 A | 12/2000 | Lassen et al. | | |
| 6,264,642 B1 | 7/2001 | Kuen et al. | | |
| 6,293,933 B1 | 9/2001 | Ahlstrand | | |
| 6,413,248 B1 * | 7/2002 | Mizutani | A61F 13/47218 | 604/385.17 |
| 6,441,268 B1 * | 8/2002 | Edwardsson | A61F 13/532 | 604/378 |
| 6,459,016 B1 | 10/2002 | Rosenfeld et al. | | |
| 6,498,283 B1 * | 12/2002 | Wada | A61F 13/4946 | 604/358 |
| 6,521,811 B1 * | 2/2003 | Lassen | A61F 13/4704 | 604/378 |
| 6,562,017 B1 | 5/2003 | Nakaoka et al. | | |
| 6,605,752 B2 | 8/2003 | Magnusson et al. | | |
| 6,617,490 B1 * | 9/2003 | Chen | A61F 13/15707 | 604/379 |
| 6,667,424 B1 * | 12/2003 | Hamilton | A61F 13/15 | 604/360 |
| 6,673,418 B1 | 1/2004 | DeOlivera et al. | | |
| 6,703,538 B2 | 3/2004 | Lassen et al. | | |
| 6,765,125 B2 | 7/2004 | Abuto | | |
| 6,844,482 B2 | 1/2005 | Eliasson | | |
| 6,867,345 B2 | 3/2005 | Shimoe et al. | | |
| 6,974,891 B2 | 12/2005 | Wallstrom | | |
| 7,078,583 B2 | 7/2006 | Kudo et al. | | |
| 7,122,023 B1 * | 10/2006 | Hinoki | A61F 13/47227 | 604/378 |
| 7,122,713 B2 | 10/2006 | Komatsu et al. | | |
| 7,294,591 B2 | 11/2007 | Soerens et al. | | |
| 7,312,372 B2 | 12/2007 | Miyama et al. | | |
| 7,578,810 B2 | 8/2009 | Rosenfeld et al. | | |
| 7,615,039 B2 | 11/2009 | Rosenfeld et al. | | |
| 7,704,241 B2 | 4/2010 | Rosenfeld et al. | | |
| 7,811,270 B2 | 10/2010 | Rosenfeld et al. | | |
| 7,883,497 B2 * | 2/2011 | Birring | A61F 13/535 | 604/365 |
| 8,029,487 B2 | 10/2011 | Bagger-Sjoback et al. | | |
| 8,153,856 B2 | 4/2012 | Wallstrom et al. | | |
| 8,247,639 B2 | 8/2012 | Itoi et al. | | |
| D673,672 S | 1/2013 | Dieringer et al. | | |
| 8,574,209 B2 | 11/2013 | Nishitani et al. | | |
| 9,066,837 B2 | 6/2015 | Kim et al. | | |

(56) References Cited

U.S. PATENT DOCUMENTS

| | | | |
|---|---|---|---|
| 9,233,185 B2 | 1/2016 | Noda et al. | |
| 9,433,542 B2 | 9/2016 | Kato et al. | |
| 9,687,392 B2 | 6/2017 | Bewick Sonntag et al. | |
| 9,730,844 B2 | 8/2017 | Miura et al. | |
| 2003/0083631 A1* | 5/2003 | Chen | A61F 13/47218 604/380 |
| 2003/0088229 A1* | 5/2003 | Baker | A61F 13/53717 604/385.101 |
| 2003/0120237 A1* | 6/2003 | Guidotti | A61F 13/15203 604/380 |
| 2003/0135177 A1* | 7/2003 | Baker | A61F 13/15634 604/368 |
| 2003/0135178 A1* | 7/2003 | Hansen | A61F 13/535 604/368 |
| 2003/0236510 A1* | 12/2003 | Yasumura | A61F 13/15626 604/367 |
| 2004/0102752 A1* | 5/2004 | Chen | A61F 13/4751 604/378 |
| 2004/0193129 A1* | 9/2004 | Guidotti | A61F 13/535 604/378 |
| 2004/0243082 A1* | 12/2004 | Kinoshita | A61F 13/4704 604/380 |
| 2004/0254554 A1* | 12/2004 | Mavinkurve | A61F 13/4756 604/380 |
| 2005/0119631 A1 | 6/2005 | Giloh et al. | |
| 2005/0137552 A1 | 6/2005 | Hansson et al. | |
| 2006/0058762 A1* | 3/2006 | Yang | A61F 13/15203 604/380 |
| 2006/0105075 A1* | 5/2006 | Otsubo | A61F 13/15626 425/363 |
| 2006/0116652 A1* | 6/2006 | Miura | A61F 13/15203 604/380 |
| 2006/0184150 A1* | 8/2006 | Noel | A61F 13/15203 604/383 |
| 2006/0206072 A1 | 9/2006 | Malakouti et al. | |
| 2006/0276767 A1* | 12/2006 | Ueminami | A61F 13/4702 604/385.31 |
| 2008/0097366 A1 | 4/2008 | Mathews | |
| 2008/0103467 A1* | 5/2008 | Wallstrom | A61F 13/47218 604/380 |
| 2009/0112175 A1* | 4/2009 | Bissah | A61F 13/535 604/385.101 |
| 2009/0270825 A1* | 10/2009 | Wciorka | A61F 13/495 604/367 |
| 2010/0036348 A1 | 2/2010 | De Carvalho et al. | |
| 2010/0114049 A1 | 5/2010 | Noda et al. | |
| 2010/0137773 A1 | 6/2010 | Gross et al. | |
| 2010/0280474 A1* | 11/2010 | Bruzadin | A61F 13/4758 604/378 |
| 2010/0312216 A1 | 12/2010 | Periman | |
| 2012/0037327 A1* | 2/2012 | Alkmin | A61F 13/15626 162/224 |
| 2012/0220971 A1 | 8/2012 | Harada et al. | |
| 2012/0226250 A1* | 9/2012 | Sato | A61F 13/51104 604/367 |
| 2013/0090619 A1* | 4/2013 | Carbonari | A61F 13/49001 604/378 |
| 2013/0131623 A1 | 5/2013 | Kawakami | |
| 2013/0139960 A1* | 6/2013 | Maruyama | A61F 13/15626 156/227 |
| 2013/0345656 A1* | 12/2013 | Kato | A61F 13/15731 604/375 |
| 2016/0120711 A1 | 5/2016 | Zamudio et al. | |
| 2017/0027765 A1* | 2/2017 | Umemoto | A61F 13/536 |

FOREIGN PATENT DOCUMENTS

| | | |
|---|---|---|
| EP | 0597273 | 6/1998 |
| EP | 0391727 | 9/1998 |
| EP | 0687453 | 4/1999 |
| EP | 0579764 | 8/1999 |
| EP | 0786980 | 4/2001 |
| EP | 0397110 | 3/2002 |
| EP | 1006970 | 4/2002 |
| EP | 1339368 | 8/2004 |
| EP | 1568340 | 8/2005 |
| EP | 1022003 | 9/2005 |
| EP | 1637108 | 3/2006 |
| EP | 1637109 | 3/2006 |
| EP | 1013252 | 1/2007 |
| EP | 2130521 | 12/2009 |
| EP | 2277484 | 1/2011 |
| EP | 1196122 | 11/2011 |
| EP | 1568341 | 9/2013 |
| EP | 1898855 | 6/2014 |
| EP | 2034942 | 10/2014 |
| EP | 1901693 | 4/2015 |
| EP | 3005999 | 4/2016 |
| EP | 2478881 | 10/2016 |
| EP | 2832326 | 1/2017 |
| EP | 2611402 | 8/2017 |
| JP | 2006116036 A * | 5/2006 |
| JP | 2012187354 A | 10/2012 |
| WO | WO-2011155460 A1 * | 12/2011 ....... A61F 13/15626 |
| WO | WO 2012/118214 | 9/2012 |
| WO | WO 2012/124378 | 9/2012 |
| WO | WO-2012124378 A1 * | 9/2012 ........... A61F 13/534 |
| WO | WO 2016/157653 | 10/2016 |
| WO | WO 2017/151093 | 9/2017 |

\* cited by examiner

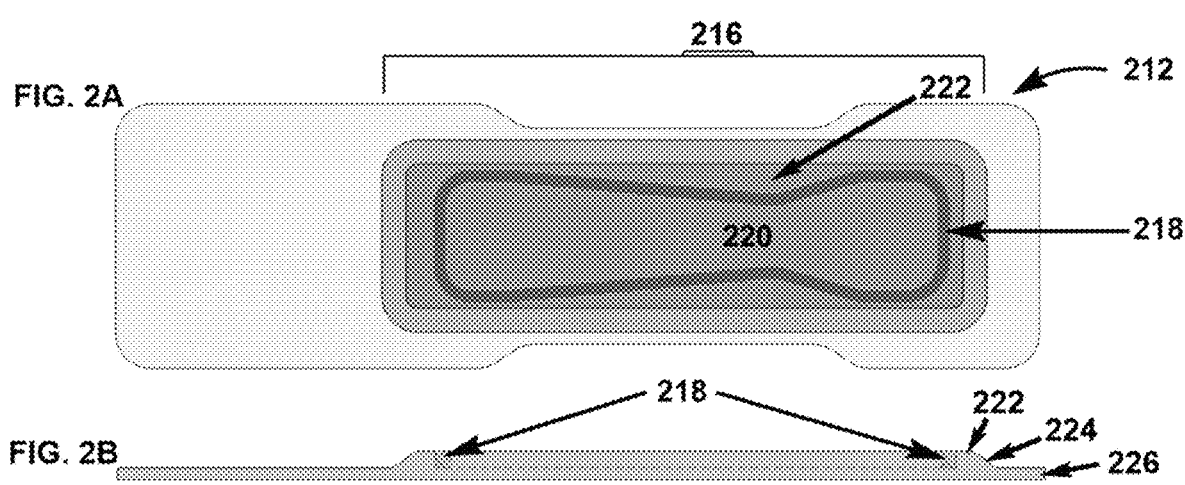

Density Profile
  Density Gradient
  Compressed Pad Profile
  Un-compressed Pad Profile

FIG. 7A

| | | Test Series I |
|---|---|---|
| ND I | LZ I | |
| 1589 | 1599 | Total Number of Diaper Changes |
| 10.1% | 7.5% | Observed Leakage |
| 4.2% | 2.5% | Observed Leakage at Front Waist |
| 4.6% | 3.6% | Observed Leakage at Leg Opening |
| 0.4% | 0.4% | Observed Leakage at Back Waist |
| 0.9% | 1.0% | Observed Leakage at Multiple Locations |
| 5.0% | 3.6% | Leakage Observed was Slight |
| 3.7% | 2.8% | Leakage Observed was Moderate |
| 1.3% | 0.9% | Leakage Observed was Severe |

FIG. 7B

| | | Test Series II |
|---|---|---|
| ND II | LZ II | |
| 1385 | 1485 | Total Number of Diaper Changes |
| 7.1% | 6.1% | Observed Leakage |
| 1.2% | 1.7% | Observed Leakage at Front Waist |
| 4.5% | 2.7% | Observed Leakage at Leg Opening |
| 0.5% | 0.7% | Observed Leakage at Back Waist |
| 0.9% | 1.1% | Observed Leakage at Multiple Locations |
| 4.1% | 2.7% | Leakage Observed was Slight |
| 2.4% | 2.7% | Leakage Observed was Moderate |
| 0.6% | 0.7% | Leakage Observed was Severe |

ABSORBENT ARTICLE WITH FLUID CONTROL FEATURES

CROSS-REFERENCE TO RELATED APPLICATIONS

This application claims the benefit of U.S. patent application Ser. No. 61/943,038, filed on Feb. 21, 2014, and No. 62/062,409, filed Oct. 10, 2014, each of which are herein incorporated by reference in their entirety.

FIELD OF THE INVENTION

Embodiments herein relate generally to disposable absorbent articles. Particularly, embodiments relate to absorbent articles having an absorbent core with a low-density zone that aids in preventing fluid leakage beyond the confines of the absorbent core.

BACKGROUND

Disposable absorbent articles include disposable diapers, disposable pull-on garments, adult incontinence articles, sanitary napkins and the like. The primary fluid-retentive component of a disposable absorbent article is the absorbent core. Absorbent cores function by absorbing waste fluid, distributing the fluid within the absorbent core, and storing the fluid to prevent leakage. Manufacturers often focus on fluid absorption near the insult area, that is, the area where exudates are likely to make first contact with the absorbent article. Absorbent cores should quickly absorb discharged fluid, so as to prevent liquid migration outside of the absorbent area and subsequent leakage. When fluid is introduced at a faster rate than can be absorbed by a conventional core, the fluid flows over the core surface and results in leakage.

The majority of absorbent cores on the market comprise structures that are uniform across the lateral and longitudinal absorbent core dimensions. These conventional absorbent cores are inexpensive to produce and require fewer manufacturing steps, and therefore, are ubiquitously employed.

In efforts to improve the fluid absorption rate, manufacturers have produced non-uniform absorbent cores with zones of low-density at the insult area. U.S. Pat. Nos. 4,834,735 and 5,047,023 disclose absorbent articles with a lower-density acquisition zone in the absorbent members. The acquisition zone is positioned in the insult area and includes a lower average density than the surrounding storage zone. Fluid pooling in the lower average density acquisition zone combined with continued waste fluid release cause discomfort to the wearer and exacerbate skin irritation associated with persistent wetness.

U.S. Pat. No. 5,134,007 discloses an absorbent article with a central acquisition zone of lower average density than the other areas of the absorbent core. The acquisition zone is surrounded by a higher-density storage zone. The absorbent core further comprises a liquid handling layer positioned subjacent at least the acquisition zone of the first layer, and a storage zone positioned subjacent the liquid handling layer. The positioning of the lower average density acquisition zone in the insult region often causes waste fluid pooling and leads to wearer discomfort after multiple insults.

U.S. Pat. No. 5,348,547 discloses a multi-layer absorbent member with a deposition region. The deposition region is positioned between a front end region and a back section. The absorbent member includes a storage layer comprising a mixture of hydrophilic fibers and absorbent gelling material. An acquisition layer is positioned in fluid communication with the storage layer and comprises curled cellulose fibers. The acquisition layer comprises two zones, an acquisition zone with a first, lower-density positioned near the insult region and a higher-density storage zone. The positioning of the lower-density acquisition zone in the insult region causes waste fluid pooling and leads to wearer discomfort after multiple insults.

U.S. Pat. No. 5,849,002 discloses an absorbent article with a triple-zone absorbent core. The first, innermost zone is a low-density zone in the insult region. The second zone is a higher density storage zone that surrounds the first zone. The third, outermost zone is an anti-leakage zone of lower density than the storage zone which it encircles. The positioning of the innermost low-density zone in the insult region causes waste fluid pooling and leads to wearer discomfort after multiple insults U.S. Pat. No. 6,974,891 discloses an absorbent article with an absorbent core made of superposed layers. The absorbent core comprises first, second, and third superposed strips. The density of the composite absorbent core is highest in the central area with three superposed strips, and lowest in the outer area with a single, non-superposed strip. The dense, central area with three superposed strips creates a relatively stiff and heavy area in the area that is in contact with the wearer, leading to wearer discomfort.

U.S. Pat. No. 6,867,345 discloses a sanitary napkin absorbent article with indented or compressed, high-density regions. The indentations divide the core into a central region between the indentations and two outer regions. The indented regions are arranged along two lines that extend longitudinally on opposites sides of the absorbent core. The rigidity of the core along the indented regions is low enough to facilitate folding, which may lead to unwanted void spaces if incorporated into any other type of absorbent article.

The uniformity of conventional absorbent cores results in absorbent structures with unvarying fluid uptake, transport and storage properties. Manufacturers have employed areas of varying-density in attempts to improve fluid dynamics; however, currently-available designs need improvement because they cause insult area pooling, require the inclusion of additional materials, allow for leaking, do not allow for sufficiently rapid intake, do not remove fluid from the top surface quickly enough, and do not redirect enough fluid to areas of the core that are previously unused. There is a need for an absorbent core with specialized areas designed to improve fluid absorption, distribution and retention, and that does not require additional production materials. The preferred embodiments discussed below seek to address some of these disadvantages of conventional absorbent cores.

SUMMARY OF THE INVENTION

Embodiments described herein relate to an absorbent core with at least one low-density zone, and methods for making the absorbent core. The low density zone is lower in density and basis weight as compared to other portions of the absorbent core. The absorbent core low-density zone is surrounded by zones of higher density, as compared to the density of the low-density zone. Further, the low-density zone has a lower basis weight as compared to the higher-density zone or zones surrounding the low-density zone. In embodiments, a higher basis weight zone (which may also have a higher density) is located in the insult area and the low-density zone surrounds that higher basis weight zone, which is surrounded by another higher basis weight zone.

In embodiments, the absorbent core's low-density zone is a continuous low-density zone. In further embodiments, the continuous low-density zone comprises a continuous channel. In other embodiments, the low-density zone is a discontinuous low-density zone. In particular embodiments, the discontinuous low-density zone comprises at least one discontinuous channel.

Methods for producing an absorbent core having variable density zones, including a low-density zone, include the steps of: providing a first forming pocket with at least one raised area, filling the first forming pocket with forming material to form an absorbent core in the shape of the first forming pocket and removing the absorbent core. The at least one raised area creates at least one impression in the absorbent core. An impression is a low basis weight zone, that when compressed to the same thickness as the surrounding materials, becomes an area of lower density, or a low-density zone.

The absorbent core may comprise a single layer or a plurality of layers. Methods for producing multiple-layer absorbent cores having variable density areas include the steps of: providing a first forming pocket with at least one raised area, filling the first forming pocket with forming material to form a first absorbent core layer in the shape of the first forming pocket, providing a second forming pocket, filling the second forming pocket with forming material to form a second absorbent core layer in the shape of the second forming pocket, removing the second absorbent core layer, and combining the second absorbent core layer with the first absorbent core layer, and, optionally, compressing the combined layers to give a multiple-layer absorbent core having at least one low-density zone. Embodiments of multiple-layer absorbent cores may include one or more base cores and one or more target cores, as will be explained below. First and/or second forming pockets may comprise a screen. A vacuum may be applied below the first and/or second screens to hold the forming material in place. Prior to filling the first and/or second forming pockets with forming material, a substrate may be applied to the first and/or second forming pockets. The substrate may be used to extract the absorbent core and/or absorbent core layer from the first and/or second forming pockets. The substrate may be wrapped around at least a part of the absorbent core and/or absorbent core layer.

The single-layer and multiple-layer absorbent cores may undergo further processing. The absorbent core may remain uncompressed or may be compressed to alter the core thickness. The absorbent core may be compressed to uniform or variable, non-uniform thickness.

The absorbent core may comprise a continuous channel or a discontinuous channel. The absorbent core may comprise one or more low-density zones. In embodiments, a low-density zone surrounds a higher-density zone located at an insult area. The low-density zone may then be surrounded by a higher-density zone.

In embodiments, forming material used in producing an absorbent core with a low-density zone comprises a mixture of SAP and cellulose fibers. In some embodiments, forming material mixtures comprises from about 5% to about 80% SAP. In further embodiments, forming material mixtures comprises from about 20% to about 65% SAP. For example, the forming material mixture may comprise about 55% SAP and about 45% cellulose fibers. The forming material may also include tow, synthetic staple fibers, bamboo fibers, coconut fibers, hemp fibers, miscanthus fibers, any combination thereof, or the like, if desired.

The low-density zone facilitates the distribution of fluids within the core to efficiently utilize the absorbent components of the article.

In order to maintain fluid absorptive capacity, fluids are diffused away from the insult area toward other areas of the absorbent core for storage, thereby reducing liquid waste concentration near the insult area.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

FIG. 2A is a top view of an absorbent core embodiment formed in one forming pocket. FIG. 2B is a side view of the absorbent core. FIG. 2C depicts the density profile along the longitudinal length of the absorbent core; FIG. 2D depicts the density gradient FIG. 2E represents a compressed absorbent core profile; FIG. 2F represents an un-compressed absorbent core profile.

FIGS. 7A and 7B are tables comparing leakage occurrences observed in use tests for absorbent articles that include an absorbent core with a low-density zone (LZ) and without a low-density zone (ND).

DETAILED DESCRIPTION

Various features and advantageous details are explained more fully with reference to the nonlimiting embodiments that are illustrated in the accompanying drawings and detailed in the following description. It should be understood, however, that the detailed description and the specific examples, while indicating embodiments, are given by way of illustration only, and not by way of limitation. Various substitutions, modifications, additions, and/or rearrangements within the spirit and/or scope of the underlying inventive concept will become apparent to those of ordinary skill in the art from this disclosure.

In the following description, numerous specific details are disclosed to provide a thorough understanding of the present embodiments. One of ordinary skill in the relevant art will recognize, however, that the embodiments may be practiced without one or more of the specific details, or with other methods, components, materials, and so forth. In other instances, well-known structures, materials, or operations are not shown or described in detail to avoid obscuring aspects of the embodiments.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed. Metric units may be derived from the English units provided by applying a conversion and rounding to the nearest millimeter.

Figure 1:
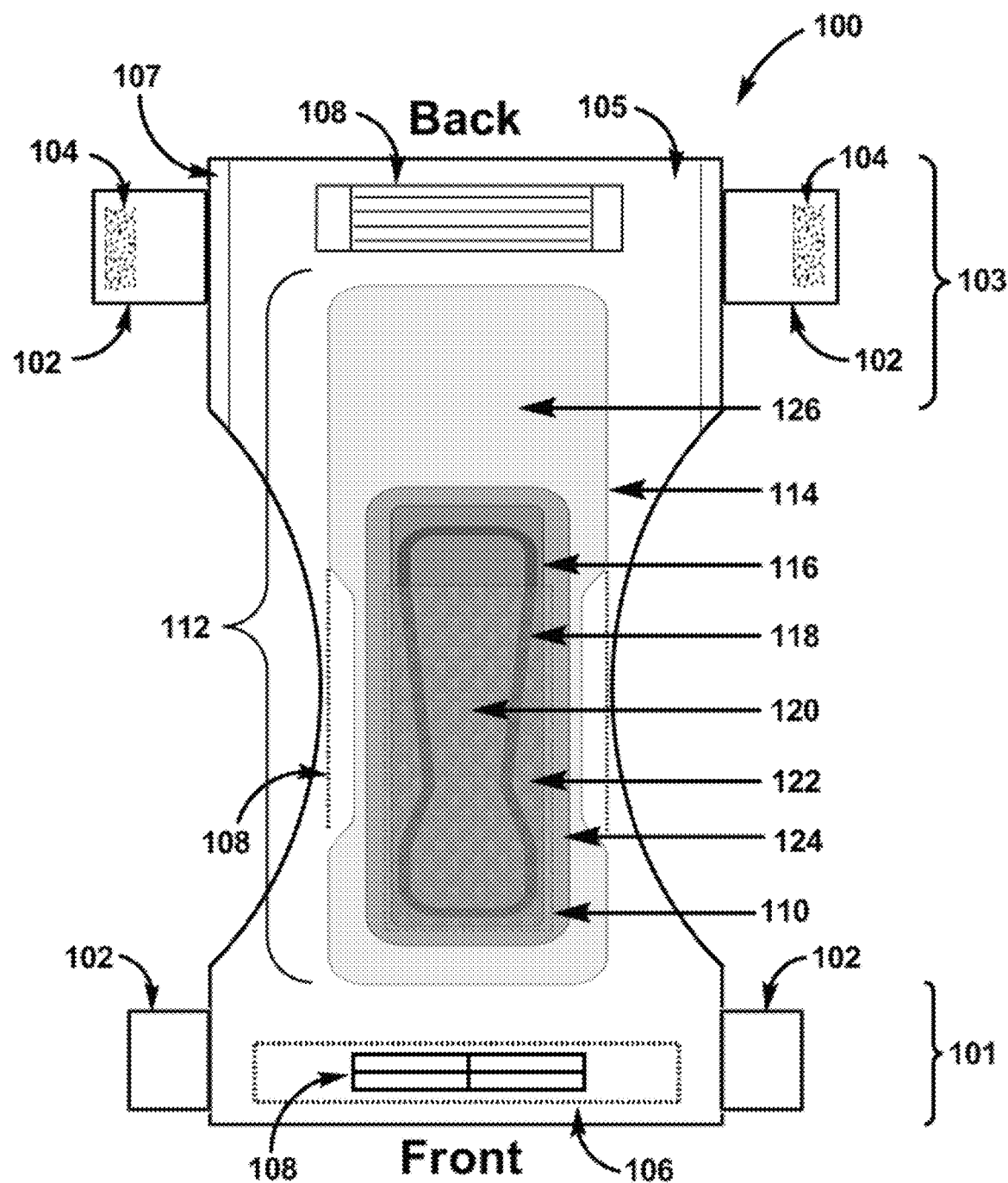
FIG. 1 depicts an absorbent article comprising an embodiment of an absorbent core.

The embodiment illustrated in FIG. 1 represents an absorbent article in the form of a diaper for children. It should first be noted that, upon review of the detailed description and the drawings provided herein, it will become apparent to one of ordinary skill in the art that the absorbent article disclosed herein is also applicable to other disposable absorbent articles, including, but not limited to, feminine care sanitary pads, training pants and adult incontinence articles.

Other features and associated advantages will become apparent with reference to the following detailed description of specific embodiments in connection with the accompanying drawings.

FIG. 1 illustrates an embodiment of a disposable absorbent article 100. The disposable absorbent article 100 can be placed against or in proximity to the body of a wearer so as to absorb and contain various bodily exudates. Absorbent article 100 is shown in the unfastened configuration and includes a front waist region 101 and a back waist region 103. The shape of absorbent article 100 may vary, and includes a generally rectangular shape, a T-style shape, an I-style shape, an hourglass shape, a combination of these shapes, and the like.

Disposable absorbent article 100 may comprise an absorbent core 112 having a central zone 120, low-density zone 118, and a perimeter zone 122. Central zone 120 encompasses one or more insult areas and is a higher-density zone having a higher basis weight and density as compared to low-density zone 118. The higher basis weight and density allows for larger storage capacity and greater capillary force, leading to fluid transportation and distribution. Central zone 120 operates as a storage portion of absorbent core 112.

Low-density zone 118 is positioned along the perimeter of central zone 120 and is a lower-density zone having a lower basis weight and density as compared to central zone 120. The lower basis weight and density provides higher void space and more porosity as compared to central zone 120, thereby allowing for quicker fluid acquisition while maintaining a relatively low capillary force. Low-density zone 118 allows fluids entering absorbent core 112 that are in excess to the storage capacity or distribution capabilities of central zone 120, or are otherwise surging, to be quickly acquired by low-density zone 118 and redistributed to other portions of absorbent core 112. For example, fluid acquired by low-density zone 118 may be redirected to un-wetted portions and/or un-saturated portions of central zone 120 and/or other un-wetted portions and/or un-saturated portions absorbent core 112.

In the example embodiment of FIG. 1, absorbent core 112 also includes perimeter zone 122 surrounding the outside of low-density zone 118. Perimeter zone 122 is a higher-density zone having a higher basis weight and density as compared to low-density zone 118. Due to having a higher basis weight and density, perimeter zone 122 may have similar fluid storage and distribution characteristics to that of central zone 120. Low-density zone 118, acquiring fluid from central zone 120, or from the surface of the absorbent core, may distribute some or all of the acquired fluid to perimeter zone 122, and to previously unused portions of central zone 120. Since perimeter zone 122 is of higher density as compared to low-density zone 118, perimeter zone 122 is capable of storing more fluid as compared to low-density zone 118. In embodiments, perimeter zone 122 may be of higher density, lower density, or the same density as compared to central zone 120.

In embodiments, absorbent core 112 may also comprise outboard zone 126. The density and/or basis weight of outboard zone 126 may be less, the same, or more as compared to perimeter zone 122. In an exemplary embodiment, the density of outboard zone is maintained similar to that of perimeter zone 122, and the basis weight of outboard zone 126 is less as compared to perimeter zone 122. Fluid within perimeter zone 122 may be distributed to and stored within outboard zone 126.

In some embodiments, for example, in single-layered absorbent cores, absorbent core 112 may include transition zone 124, which is located between perimeter zone 122 and outboard zone 126. Transition zone 124, while maintaining density, may gradually decrease in basis weight as it transitions from perimeter zone 122 to outboard zone 126.

Low-density zone 118 may comprise one or more channels inside the perimeter of absorbent core 112. In some embodiments, low-density zone 118 is a continuous low-density zone having a single channel, as represented by the uninterrupted low-density zone 118 in FIG. 1. FIGS. 2A, 3A, 4A, and 4B likewise illustrate continuous low density zones (e.g., 218, 318, 418, and 438) having a single channel. In embodiments, some or all low-density zones may be discontinuous. FIG. 4C is an example of absorbent core 452 with a discontinuous low-density zone 458 (dark regions 458a-458h). Low-density zone 458 may have varying low-density zones, as is desired. For example, low-density zone 458a may be of a different density as compared to low density zone 458b. Further, low-density zone 458a may have varied low-density therein. Varying the density of low-density portions may be used to promote controlled fluid flow in a particular direction, at a particular rate, and/or the like.

A variety of discontinuous low-density zone designs are contemplated. In one embodiment, a discontinuous low-density zone comprises a single channel that is interrupted by a single area of high density. In other embodiments, a discontinuous low-density zone is interrupted by two or more areas of higher density. In further embodiments, a discontinuous low-density zone comprises areas of low density that are assembled into a pattern. Non-limiting examples of discontinuous low-density zone patterns include a tessellation, one or more meanders, a dotted line, a dashed line, a checkerboard pattern, and/or the like. In yet other embodiments, a discontinuous low-density zone comprises two or more areas of low density that are seemingly randomly-oriented, and do not resemble a discernible pattern.

Low-density zone 118 allows for rapid acquisition of fluids. Fluids entering absorbent core 112 that are either in excess of the local capacity or are a surge to central area 120 and flow through or across the surface of central zone 120 can be quickly acquired by surrounding low-density zone 118 and redirected to other, and possibly un-wetted, portions of the absorbent core.

Low-density zone 118 may exhibit high void space, open porosity and display relatively low capillary force capable of acquiring and transporting comparatively higher fluid volumes over shorter distances. Low-density zone 118 offers both a transient and permanent fluid storage space. Fluids absorbed directly into the low-density zone may be redirected to drier, higher basis weight areas (which may also have higher density) that are capable of transporting comparatively lower volumes with greater force and that are adjacent to low-density zone 118 by capillary forces. Fluids migrating or wicking internally in absorbent core 112 that reach the saturation point are redirected by low-density zone 118 to areas of absorbent core 112 that were previously unused or underused. Upon saturation of the surrounding, higher basis weight (which may be higher density) core areas, the void space of low-density zone 118 may also store excess fluid.

The absorbent core 112 may comprise one or more constituent core layers. In preferred embodiments, the absorbent core 112 comprises one or more base core 114 and one or more target core 116. In embodiments, either or both of base core 114 and target core 116 may comprise one or more low-density zone 118. The base core 114 and target core 116 may be formed separately then coupled to produce absorbent core 112. In other embodiments, base core 114 and target core 116 may be integrally-formed. In particular preferred embodiments, the target core 116 lies between base core 114 and topsheet 105. In some embodiments, the base core 114 and target core 116 are compressed to give an absorbent core 112 a substantially uniform density across areas 120, 122, 124, and 126. In other embodiments, absorbent core 112 remains in an uncompressed state. Absorbent core 112 may be positioned within absorbent article 100 such that base core 114 or target core 116 faces the wearer.

In some aspects of the invention, methods for the production of absorbent cores with one or more low-density zone are provided. In preferred embodiments, absorbent cores are formed in a forming pocket or mold. The forming pocket may comprise a recess configured to receive forming material (such as a mixture of pulp and superabsorbent polymer particles (SAP)) and a raised area, rising inside the recess that corresponds to the low-density area on the absorbent core. In some embodiments, an absorbent core is produced in a single absorbent core-forming pocket. In other embodiments, absorbent cores are produced in multiple absorbent core-forming pockets then combined to give a composite absorbent core. Production of the absorbent cores includes the step of filling at least one forming pocket with forming material. The forming material fills the forming pocket space to yield an absorbent core in the shape of the forming pocket. In some embodiments, forming material is uniformly deposited into the forming pocket to a constant height. In embodiments, a comb is used to crop off the top of the deposited forming material.

In some embodiments, a combination of forming materials is used to construct absorbent cores 112, 212, 312, 412, 432, and 452. In embodiments, a mixture of cellulose fibers and superabsorbent material is used to construct absorbent core 112. A particularly-suited superabsorbent material comprises superabsorbent particles (SAP) of sodium polyacrylate. In some embodiments, the average size of the cellulose fibers is from about 1.0 mm to about 3 mm. In some embodiments, absorbent core materials are mixed with adhesive prior to absorbent core construction. Additionally or alternatively, adhesive is sprayed onto the formed forming material after deposition into the forming pocket(s).

Other suitable high-absorbency materials useful in construction of absorbent cores 112, 212, 312, 412, 432, and 452 include inorganic materials, for example, absorbent clays and silica gels. Examples of organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably highly cross-linked to impart desired levels of water insolubility to the material.

Absorbent cores may additionally comprise a variety of different materials, such as hydrophilic fibers, cellulosic fluff such as wood pulp, superabsorbent hydrogel forming particles, synthetic polymeric fibers, meltblown fibers, natural fibers, tow, or combinations thereof.

In various embodiments, the weight percentage of SAP in absorbent cores 112, 212, 312, 412, 432, and 452 may range from about 5% to about 80% and, more preferably, from about 20% to about 65%. In specific embodiments, the percentage of SAP in absorbent core 112 comprises 55% SAP. In any of these embodiments, the remaining weight percentage of absorbent core 112 can comprise cellulosic pulp (also known as fluff) and/or adhesive, binders, other fibers, foams, and combination thereof, and or the like.

Example absorbent article 100 also may also include one or more acquisition distribution layer (ADL) 110. ADL 110, which may be a nonwoven such as through air bonded, thermo-bonded, or resin bonded nonwoven, any combination of spunbond-meltblown nonwoven, spunbond-meltblown-spunbond nonwoven, or a polymeric film, such as a film formed from polypropylene, polyester or polyethylene, including aperture film, perforated film, reticulated/open-celled foam, any combination thereof, and/or the like. ADL 110 may be a sublayer placed between the topsheet 105 and absorbent core 112. ADL 110 may distribute liquid over a larger surface area in order to increase saturation capacity of absorbent article 100.

Referring again to FIG. 1, disposable absorbent article 100, at the front 101 and/or back 103 waist regions may include tab portions or protrusions 102 extending generally perpendicular to the longitudinal centerline at waist regions 101 and 103. In this way, the front and back waist regions may be brought together and attached at the tab portion to form, in combination with portions of the article chassis, openings to accommodate the wearer's legs. The shapes and configurations of tab portions 102 may be formed in any manner to accomplish the particular purposes of disposable garment 100. For example, tab portions 102 may be configured to be permanently or refastenably attached. Additionally, tab portions 102 may be known as side panels. The tab portions 102 may be made of an elastic or extensible material or comprise at least a portion of an elastic or extensible material. Tab portions 102 may be attached to topsheet 105 or backsheet 107 or may be sandwiched between topsheet 105 and backsheet 107.

Disposable absorbent article 100 also comprises fastening means, or fasteners, 104 to attach the front 101 and back 102 waist regions of the garment together. Examples of fasteners 104 may include hook and loop fasteners, buttons, pins, snaps, adhesive tape fasteners, cohesives, mushroom and loop fasteners, or the like. The fasteners 104 may be attached to tab portions 102 or integrated onto topsheet 105 or backsheet 107.

More specifically, loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are known in the art and are available, for example, from manufacturers such as 3M, St. Paul Minn. (designated as a KN series loop). The loop material can be an integral portion of the outer surface or inner surface of the side panel rather than a separated material or structure.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for fasteners 104 are known in the art and are available, for example, from manufacturers such as 3M, St. Paul Minn. (designated as a CPL series loop).

Fasteners 104 may be located at the front 101 or back 103 waist region of absorbent article 100, or at both. For example, in the representative embodiment of FIG. 1, fasteners 104 are attached to tab portions 102 located on the back waist region 103, and are configured to engage with fastening means on tab portions 102 located on the front waist region 101 of disposable absorbent article 100. In other embodiments, fasteners 104 on the back waist region 103 may engage with a corresponding fastening region 106 on front waist region 101.

Additionally, absorbent article 100 may comprise elastic portions to help conform the absorbent diaper to the wearer's body. For example, generally some part of front 101 and/or back 103 waist regions may comprise elastic material 108 to aid in fitting the garment to the wearer's waist. Also, both sides of the crotch region may comprise elastic material 108 to fit the garment to the wearer's legs, and to provide sealing means to keep any extra liquid or exudate inside of the absorbent article. Suitable material for use as elastic members are well known to those skilled in the art. An embodiment of elastic material construction includes sheets or strands of ribbons of polymeric, elastomeric material adhered to a sheet in the extended configuration. These elastic members may include polyurethane, synthetic rubber, natural rubber, or any combination thereof. Exemplary embodiments of elastic members that may be used with the present invention are given in U.S. Pat. No. 4,892,536 issued Jan. 9, 1990 to DesMarais et al., U.S. Pat. No. 5,540,796 issued Jul. 30, 1996 to Fries, U.S. Pat. No. 4,895,568 issued Jan. 23, 1990 to Enloe, and U.S. Pat. No. 5,196,000 issued Mar. 23, 1993 to Clear et al.

The absorbent article may additionally include cuffs or flaps that run along the longitudinal centerline close to the leg edge of the absorbent article. These cuffs provide extra sealing to keep excess fluids and material inside of the absorbent article. The cuffs may have additional elastic, e.g., elastic 108, in them to better fit the wearer, and may also comprise absorbent material to prevent leakage. Exemplary embodiments of cuffs are given in U.S. Pat. No. 5,584,828 issued Dec. 17, 1996 to Yamamoto, U.S. Pat. No. 5,827,387 issued Oct. 27, 1998 to Reynolds, U.S. Pat. No. 6,264,642 issued Jul. 24, 2001 to Kuen, and U.S. Pat. No. 6,562,017 issued May 13, 2003 to Nakaoka, et al.

The various components of the absorbent article, e.g., topsheet 105, ADL 110, absorbent core 112, elastic portions 108, and tab portions 102, etc., are integrally assembled together using various types of suitable attachment means that are well known in the art. These attachments means include the non-limiting examples of adhesives, sonic bodying, thermal boding, or any combination thereof.

Backsheet 107 is generally that portion of absorbent article 100 positioned adjacent the garment facing surface of absorbent core 112 which prevents the exudates absorbed and contained therein from soiling articles that may contact absorbent article 100. In preferred embodiments, backsheet 107 is impervious to liquids (e.g., urine) and comprises a thin plastic film such as a thermoplastic film having a thickness of about 0.012 mm (0.5 mils) to about 0.051 mm (2.0 mils). Backsheet 107 may be constructed of a single material or may comprise a composite material. Backsheet 107 may comprise a woven fabric, a nonwoven fabric, a polymer film, a film-fabric laminate or the like, and combinations thereof. Examples of nonwoven fabric include spunbond fabric, meltblown fabric, coform fabric, carded web, bonded carded web or the like, as well as combinations thereof. Other examples of suitable materials for constructing backsheet 107 include bonded carded webs of polyester, polypropylene, polyethylene, nylon, rayon other heat-bondable fibers, polyolefins, such as copolymers of polypropylene and polyethylene, linear low-density polyethylene, aliphatic polyesters, as well as combinations thereof. Particularly suitable backsheet films include those manufactured by Tredegar Industries Inc. of Terre Haute, Ind. and sold under the trade name X15306, X10962 and X10964.

Other suitable backsheet materials may include breathable materials which permit vapors to escape from diaper 100 while still preventing exudates from passing through backsheet 107. Exemplary breathable materials may include materials such as woven webs, nonwoven webs, composite materials such as film-coated nonwoven webs, and macroporous films such as manufactured by Mitsui Toatsu Co. of Japan under the designation ESPOIR NO and by Tredegar Corp. of Richmond, Va. under the designation EXAIRE. Suitable breathable composite materials comprising polymer blends are available from Clopay Corporation, Cincinnati, Ohio under the name HYTREL blend P18-3097.

Backsheet 107 may be joined to topsheet 105, absorbent core 112 or any other element of absorbent article 100 by any attachment means known in the art. For example, the attachment means may include a uniform continuous layer of adhesive, a patterned layer of adhesive, or an array of separate lines, spirals, or spots of adhesive. Examples of suitable adhesives comprise thermopolastic polymers such as styrenic block copolymers, amorphous and crystalline polyolefins including homogeneous and substantially linear ethylene/alpha-olefin interpolymers, interpolymers of ethylene such as ethylene-vinyl-acetate, ethylene-methyl acrylate, ethylene-n-butyl acrylate, polylactide, caprolactone polymers, poly(hydroxyl-gutyrate/hydroxyvalerate), certain polyvinyl alcohols, linear saturated polyesters, and mixtures thereof.

The adhesives may comprise additional components, such as plasticizing oils, tackifiers, fillers, pigments, antioxidants and other stabilizers. Exemplary adhesives are provided in U.S. Pat. No. 4,460,364 to Chen, issued on Jul. 17, 1984 and U.S. Pat. No. 4,136,699 to Collins, issued on Jan. 30, 1979. Adhesives which have been found to be satisfactory are manufactured by Bostik, Incorporated and include H2594 and H2561. Alternatively, the attachment means may comprise heat bonds, pressure bonds, ultrasonic bonds, dynamic mechanical bonds, or any other suitable attachment means or combinations of these attachment means as are known in the art.

Topsheet 105 is preferably positioned adjacent to the body of a user and between the user and absorbent core 112. Topsheet 105 may be joined to absorbent core 112 and/or to backsheet 107 by any attachment means suitable for such joining, such as discussed above. In some embodiments, topsheet 105 and backsheet 107 are joined directly in some locations and indirectly joined in other locations by directly joining topsheet 105 to other elements of absorbent article 100.

Topsheet 105 is preferably compliant, soft feeling, and non-irritating to the wearer's skin. Further, at least a portion of topsheet 105 is liquid pervious, permitting liquids to readily penetrate through its thickness. A suitable topsheet 105 may be manufactured from a wide range of materials, such as porous foams, reticulated foams, apertured plastic films, or woven or nonwoven webs of natural fibers (e.g., cellulosic fibers), synthetic fibers (e.g., polyester or polypropylene fibers), meltblown webs, airlaid webs, spunbond webs, a pattern bonded spunbonded web, bonded-carded webs of synthetic continuous or discrete polymer fibers and/or natural fibers, or a combination thereof. For example, one suitable topsheet 105 comprising a web of staple length polypropylene fibers is manufactured by Veratec, Inc., a Division of International Paper Company, of Walpole, Mass. under the designation P-8.

Preferably, topsheet 105 is made of a hydrophobic material or is treated to be hydrophobic in order to isolate the wearer's skin from liquids contained in absorbent core 112. If topsheet 105 is made of a hydrophobic material, preferably at least the upper surface of topsheet 105 is treated to be hydrophilic so that liquids will transfer through the topsheet more rapidly. This diminishes the likelihood that body exudates will flow off topsheet 105 rather than being drawn through topsheet 105 and being absorbed by the absorbent core 112. Topsheet 105 can be rendered hydrophilic by treating it with a surfactant or by incorporating a surfactant into the topsheet. Suitable methods for treating topsheet 105 with a surfactant include spraying the topsheet material with the surfactant and immersing the material into the surfactant. A more detailed discussion of such a treatment and hydrophilicity is contained in U.S. Pat. No. 4,988,344 issued Jan. 29, 1991 to Reising, et al. and U.S. Pat. No. 4,988,345 issued Jan. 29, 1991 to Reising. A more detailed discussion of some suitable methods for incorporating surfactant in the topsheet can be found in U.S. Statutory Invention Registration No. H1670, published on Jul. 1, 1997 in the names of Aziz et al. Alternatively, topsheet 105 may include an apertured web or film that is hydrophobic. This may be accomplished eliminating the hydrophilizing treatment step from the production process and/or applying a hydrophobic treatment to topsheet 105, such as a polytetraflouroethylene compound like SCOTCHGUARD™ or a hydrophobic lotion composition, as described below. In such embodiments, it is preferred that the apertures be large enough to allow the penetration of aqueous fluids like urine without significant resistance.

Any portion of the topsheet 105 may be coated with a lotion as is known in the art. The lotion may function alone or in combination with another agent as the hydrophobizing treatment described above. Topsheet 105 may also include or be treated with antibacterial agents. Further, topsheet 105, backsheet 107, or any portion of topsheet 105 or backsheet 107 may be embossed and/or matte finished to provide a more cloth like appearance.

FIG. 2A illustrates a single layered absorbent core 212 made using a single forming pocket. Example absorbent core 212 includes central zone 220, low-density zone 218, and perimeter zone 222. As described above, central zone 220 may comprise one or more insult areas and be of higher density as compared to low-density zone 218. Low-density zone 218 is shown as being a continuous channel that surrounds central area 220 and is of lower density as compared to central area 220. Perimeter zone 222 surrounds low-density zone 218.

In some embodiments, the density of one or more low-density zone 218 ranges from about 0.02 g/cc to about 0.18 g/cc. In some embodiments, the density of low-density zone 218 ranges from about 0.06 g/cc to about 0.14 g/cc. In preferred embodiments, the density of low-density zone 218 is about 0.10 g/cc.

In some embodiments, the density of one or more higher density zones (e.g., central zone 220 and/or perimeter zone 222) ranges from about 0.10 g/cc to about 0.26 g/cc. In some embodiments, the density of a higher density zone ranges from about 0.14 g/cc to about 0.22 g/cc. In preferred embodiments, the density of higher zone is about 0.18 g/cc.

In embodiments, the density of outboard zone 226 ranges from about 0.10 g/cc to about 0.26 g/cc Transition zone 224 between perimeter zone 222 and outboard zone 226 may have gradually decreasing density, which decreases from a density equal to the density of perimeter zone 222 to a density equal to the density of outboard zone 226.

In some embodiments, the basis weight of one or more low-density zone 218 ranges from about 200 gsm to about 700 gsm. In some embodiments, the basis weight of a low-density zone 218 ranges from about 325 gsm to about 575 gsm. In preferred embodiments, the basis weight of a low-density zone 218 is about 450 gsm. In some embodiments, the basis weight of one or more higher density zones (e.g., central zone 220 and/or perimeter zone 222) ranges from about 700 gsm to about 1,100 gsm. In some embodiments, the basis weight of a higher density zone ranges from about 800 gsm to about 1,000 gsm. In preferred embodiments, the basis weight of the higher density zone is about 900 gsm.

In embodiments, the basis weight of outboard zone 226 ranges from about 200 gsm to about 700 gsm. In some embodiments, the basis weight of outboard zone 226 ranges from about 325 gsm to about 575 gsm. In preferred embodiments, the basis weight of outboard zone 226 is about 450 gsm. Transition zone 224 between perimeter zone 222 and outboard zone 226 may have gradually decreasing basis weight, which decreases from a basis weight equal to the basis weight of perimeter zone 222 to a basis weight equal to the basis weight of outboard zone 226.

In preferred embodiments, methods for the production of absorbent cores such as those disclosed herein, with low-density zones involve a frame with a forming pocket cutout in the shape of the absorbent core being formed. The forming pocket may comprise one or more areas, which rise into the forming pocket (e.g., a raised area). In some embodiments, the raised area is a continuous raised area. In other embodiments, the raised area comprises multiple, discontinuous raised areas. This raised area may be used to form low-density zone 218 of absorbent core 212. In production, less forming material is deposited at the raised area of the forming pocket, which results in a depression, or channel, in embodiments of absorbent core 212. As explained, low-density zone 218, formed at the raised area has higher void space and a higher porosity as compared to central zone 220 and perimeter zone 222.

The forming pocket may comprise a screen on the deposition surface. A vacuum may be applied through the screen to draw and retain forming material into the forming pocket. In some embodiments, a substrate is placed over the deposition surface prior to the application of forming material. Additionally and/or alternative, the same or another substrate may be applied on top of the forming material after it has been deposited in the forming pocket.

The one or more substrate(s) may be used to aid in extraction of the absorbent core from the forming pocket or mold and may become an integral part of the absorbent core. In some embodiments, the substrate is wrapped around at least a part of the absorbent core.

In some embodiments, forming material is deposited to a height above the forming pocket frame. In other embodiments, forming material is deposited to a height such that it is flush with the forming pocket frame. In embodiments, portions of the forming material are shaved off, sliced off, cut away, and/or otherwise removed, to the appropriate height.

In the embodiment illustrated in FIG. 2A, a single forming pocket is used to form a single layer absorbent core 212. In this single layer embodiment, central zone 220, low-density zone 218, perimeter zone 222, and transition zone 224 form a target area 216, which handles most of the fluid storage. Outboard zone 226 handles fluid overflow and aids in preventing leakage. In the single layer embodiment, target area 216 and outboard zone 226 are integrally formed into a single layer absorbent core 212. The FIG. 2B Side View illustrates absorbent core 212 as a continuous region resulting from the deposition of forming material into a single forming pocket. Perimeter zone 222 is shown as meeting transition zone 224, which gradually transitions into outboard zone 226. The FIG. 2C Density Profile shows a drop in density at locations that correspond to low-density zones. The lighter-shaded areas in the FIG. 2D Density Gradient show the low-density zones of absorbent core 212 which have lower basis weight and/or density.

In embodiments, absorbent core 212 may be compressed to uniform thickness, may be left uncompressed, or may be variably compressed to variable heights, as is desired. As shown in the Compressed Pad Profile in FIG. 2E, in preferred embodiments, absorbent core 212 may be compressed to a variable thickness such that any channel or depression formed by the raised area of the forming pocket becomes a low-density area of a variable thickness core. In an alternative embodiment, as shown in the FIG. 2F Un-compressed Pad Profile, absorbent core 212 may be left un-compressed such that any channel or depression formed by the raised area of the forming pocket is left as having a height which is different from some or all other portions of absorbent core 212.

Figures 3A, 3B:
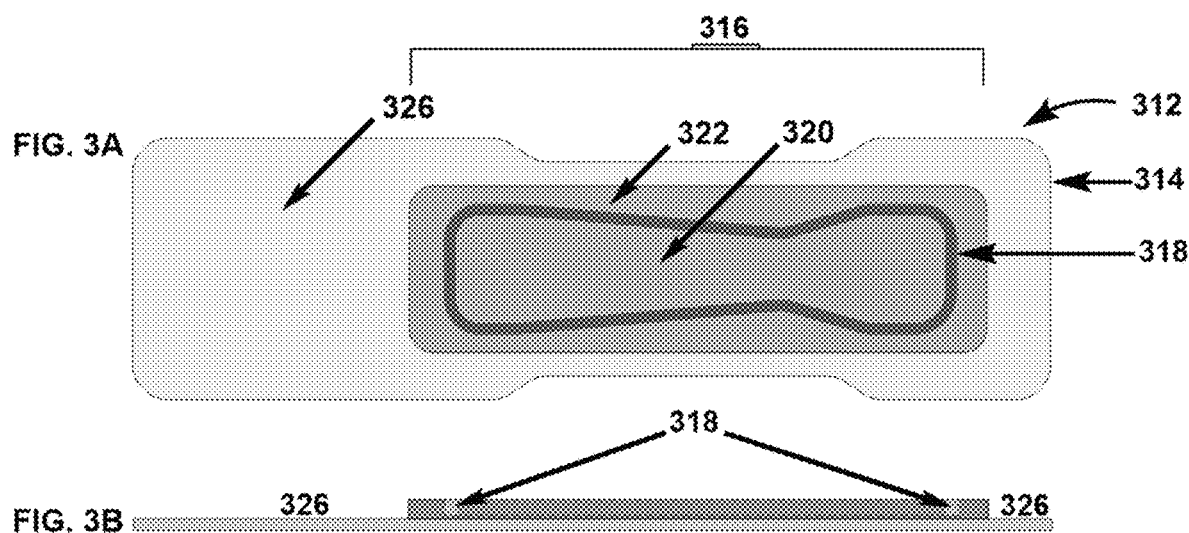
FIG. 3A is a top view of an absorbent core embodiment formed in two forming pockets.
FIG. 3B is a side view of the absorbent core.
Figure 3C:
FIG. 3C depicts the density profile along the longitudinal length of the absorbent core.
Figure 3D:
FIG. 3D depicts the density gradient
Figure 3E:
FIG. 3E represents a compressed absorbent core profile.
Figure 3F:
FIG. 3F represents an un-compressed absorbent core profile.

In the embodiment illustrated in FIG. 3A, two forming pockets are used to form a multilayer absorbent core 312. Absorbent core's 312 first layer is target core layer 316 having central zone 320, low-density zone 318, and perimeter zone 322. Target core layer 316 is formed in a first forming pocket. Absorbent core's 312 second layer is base core layer 314 having outboard zone 326. Base core layer 314 is formed in a second forming pocket. Target core layer 316 and base core layer 314 are removed from their respective forming pockets and coupled together, as illustrated in FIG. 3B Side View, forming multilayered absorbent core 312. In some embodiments, transition zone (not shown) is omitted from absorbent core 312, if desired, as is illustrated in the FIG. 3B Side View and FIG. 3F Un-compressed Pad Profile View.

Multilayered absorbent cores may include any number of layers made from any number of forming pockets. Any number of base cores and/or target cores of varying densities, weight basis, thickness, and comprising any number of low-density zones 318, perimeter zones 322 and outboard zones 326 may be combined together into an absorbent core. Further, multilayered absorbent cores may layer target core layers and base core layers in any order.

Figure 4A:
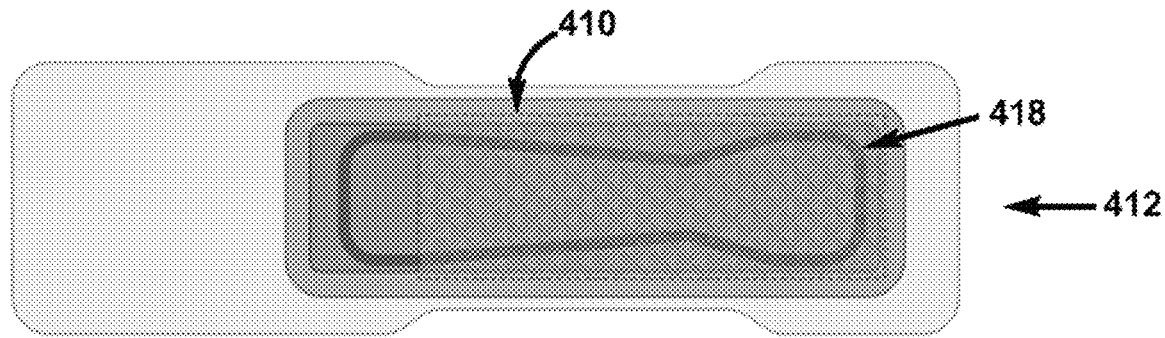
FIG. 4A is a top view of an absorbent core formed in one forming pocket with a continuous low-density zone.
Figure 4B:
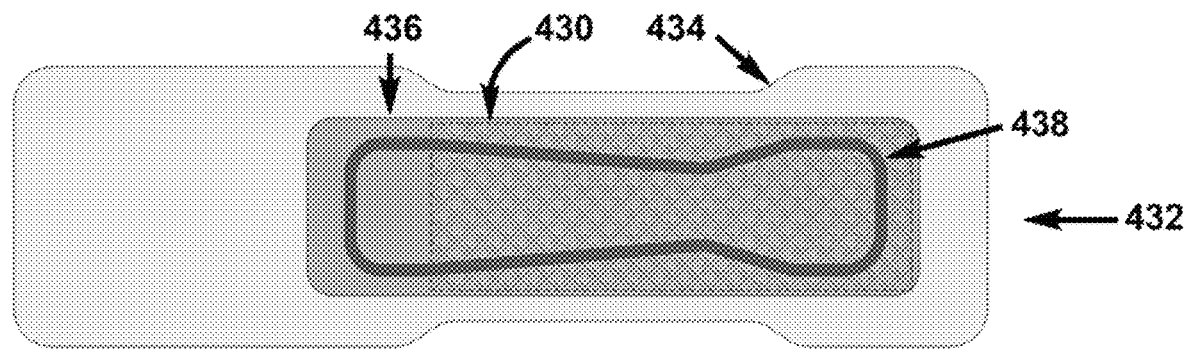
FIG. 4B is a top view of an absorbent core formed in two forming pockets with a continuous low-density zone.
Figure 4C:
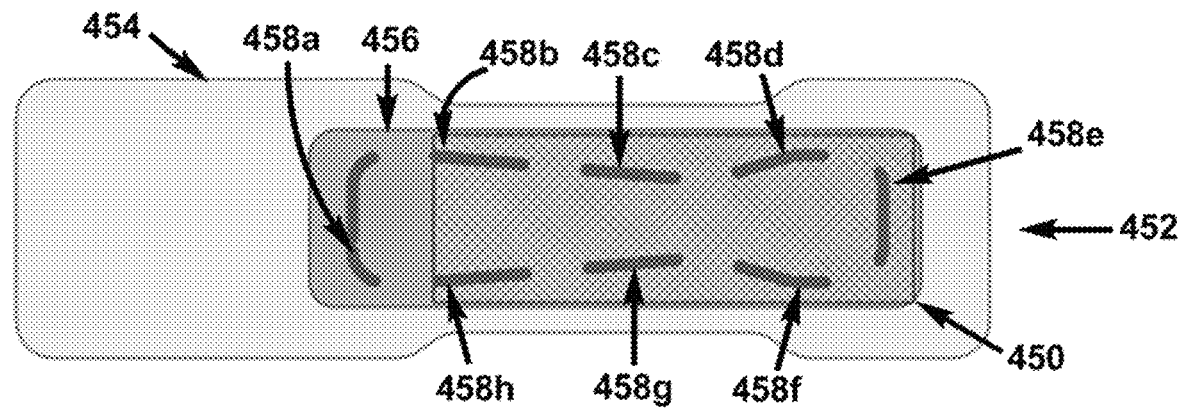
FIG. 4C is a top view of an absorbent core formed in two forming pockets with a discontinuous low-density zone.

In the embodiment illustrated in FIG. 4A, ADL 410 is positioned on top of absorbent core 412. In this embodiment, absorbent core 412 is produced by a one-pocket forming process, and includes a continuous low-density zone 418. The illustrative absorbent core 432 of FIG. 4B is produced using the above described two-pocket forming process, and comprises target core layer 436 positioned above base core layer 434. ADL 430 is positioned on above target core layer 436, as such ADL 430 is closer to the skin of the wearer of absorbent core 432 as compared to target core layer 436. Absorbent core 432, includes continuous low-density zone 438.

The embodiment illustrated in FIG. 4C shows a multi-layered absorbent core 452 with at least one target core layer 456 being positioned above at least one base core layer 454. Target core layer 456 comprises a discontinuous low-density zone 458, including low-density portions 458a-458h. Low-density portions 458a-458h may all be of the same low-densities and/or basis weights, or may all be of different densities and/or basis weights. Alternatively, any number of 458a-458h may be of the same or different densities and/or basis weights, as is desired. Above target core layer 456 is ADL 450.

Figure 5:
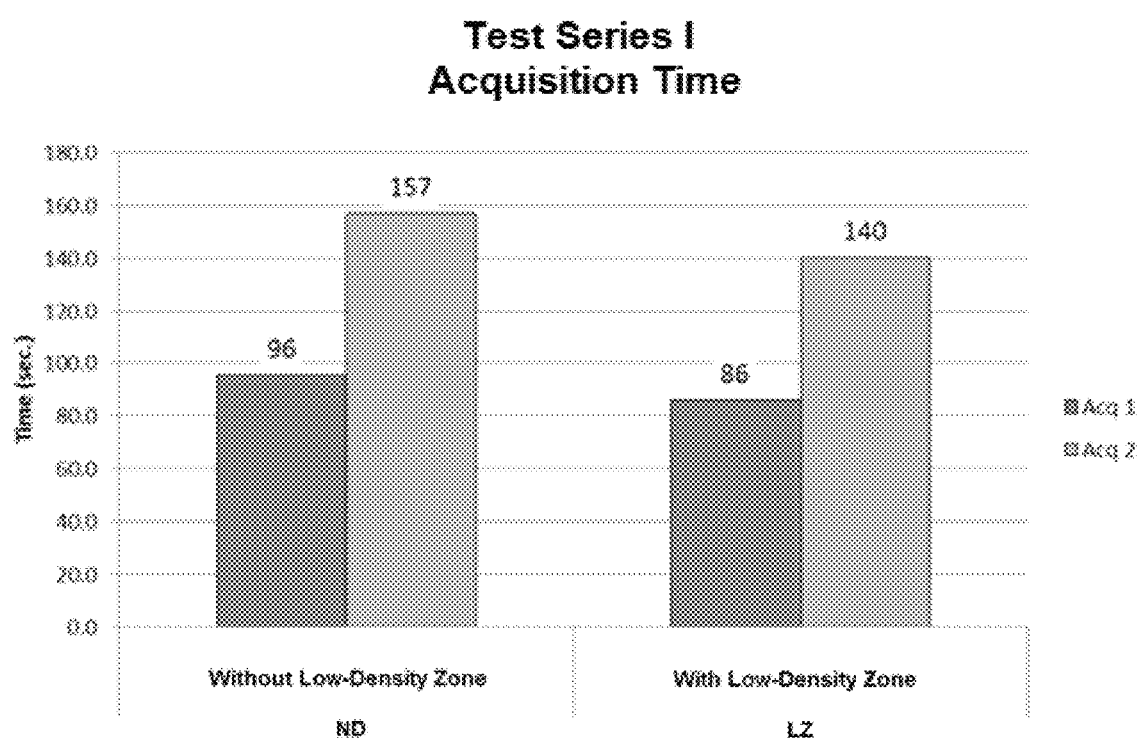
FIG. 5 is a graph comparing average acquisition times between absorbent cores with a low-density zone (LZ) and without a low-density zone (ND).

The graph in FIG. 5 compares acquisition times between absorbent cores with a low-density zone (ND), as disclosed herein, and without a low-density zone (NZ). Acquisition time relates to the speed at which fluid enters the absorbent core. Lower acquisition time reduces the opportunity for leakage. Lower acquisition time is preferred, as it reflects less free fluid on the surface of the absorbent article for a given period of time. Acquisition times were lower for absorbent articles with low-density zone absorbent cores.

Figure 6A:
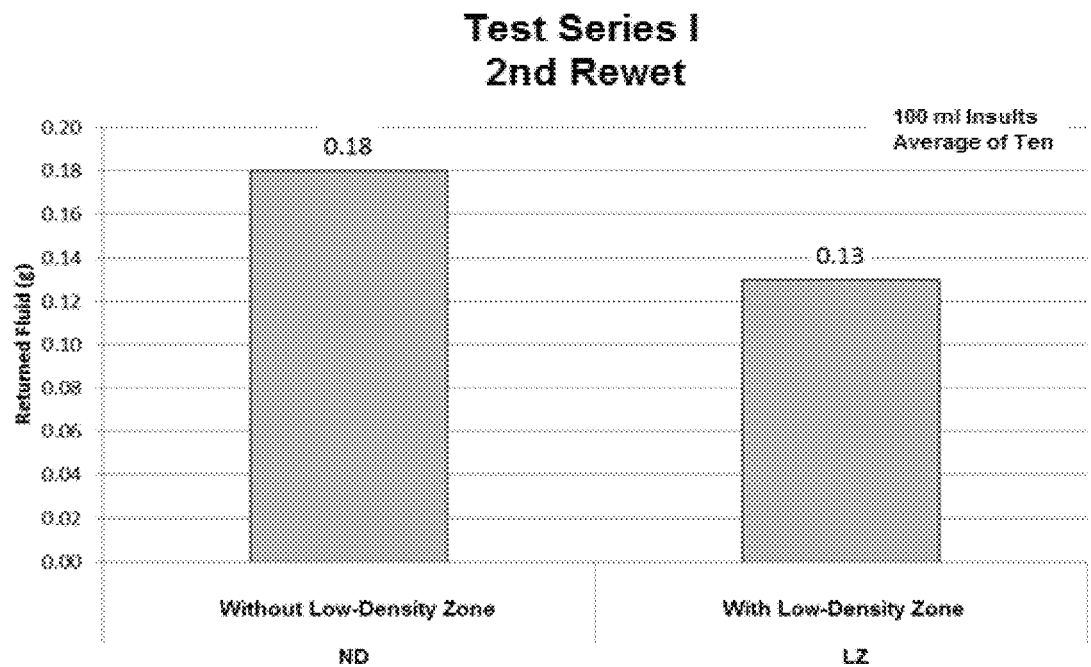
FIGS. 6A and 6B are graphs comparing the average amount of fluid that remains free (rewet) after absorbent cores with a low-density zone (LZ) and without a low-density zone (ND) have been subjected to specific and multiple liquid insults for a specific duration.
Figure 6B:

FIG. 6A is a graph comparing rewet after absorbent cores with and without a low-density zone, as disclosed herein, have been subjected to two 100 mL insults after a specific duration. The measure of rewet relates to the amount of fluid that remains free within the core and at the surface after it has been acquired by the absorbent core and after a specific duration. Low rewet is preferred as it reflects less moisture at the wearer's skin and reduced potential of dermatitis. FIG. 6A demonstrates that absorbent cores with a low-density zone exhibit significantly lower rewet than absorbent cores without a low-density zone. FIG. 6B is a graph comparing rewet after absorbent cores with and without a low-density zone have been subjected to two 80 mL insults after a specific duration. The comparison shows that absorbent cores with a low-density zone, as disclosed herein, demonstrate significantly lower rewet than absorbent cores without a low-density zone.

FIGS. 7A and 7B are tables comparing leakage occurrences from two separate use tests for absorbent articles that include an absorbent core with a low-density zone (LZ), as disclosed herein, and without a low-density zone (ND). Each test counted articles that experienced urine leakage that occurred over approximately 1,500 diaper changes for each core configuration. Articles produced under similar conditions and constructions show 25% (FIG. 7A) and 14% (FIG. 7B) reductions in leakage occurrence for articles that incorporate the low-density zone over articles that do not contain the feature.

The claims are not to be interpreted as including means-plus or step-plus-function limitations, unless such a limitation is explicitly recited in a given claim using the phrase(s) "means for" or "step for," respectively.

We claim:

1. An absorbent article comprising an absorbent core, the absorbent core comprising a mixture of cellulosic pulp and superabsorbent polymer, where the core comprising the mixture defines:
    a single central zone comprising at least one insult area;
    a single continuous low-density zone surrounding the central zone, wherein the low-density zone is lower in density as compared to that of the central zone;
    a single perimeter zone surrounding the low-density zone, wherein the perimeter zone is higher in density as compared to that of the low-density zone; and
    a single outboard zone surrounding the perimeter zone;
    wherein the central zone, perimeter zone, and the outboard zone have the same density;
    wherein the central zone, low-density zone, and perimeter zone have the same thickness; and
    wherein the outboard zone has a thickness that is less than the thickness of the central zone, low-density zone and perimeter zone.

2. The absorbent article of claim 1, wherein the absorbent core comprises a plurality of layers.

3. The absorbent article of claim 2, wherein the absorbent core comprises a base core layer.

4. The absorbent article of claim 2, wherein the absorbent core comprises a target core layer.

5. The absorbent article of claim 1, wherein a target area of the absorbent core is of uniform thickness.

6. The absorbent article of claim 1, wherein the absorbent core comprises from about 5% to about 80% SAP.

7. The absorbent article of claim 1, wherein the absorbent core comprises from about 20% to about 65% SAP.

8. The absorbent article of claim 1, wherein the absorbent core comprises about 55% SAP.

9. The absorbent article of claim 1, wherein the absorbent core comprises about 45% cellulose fibers.

10. An absorbent article comprising an absorbent core, the absorbent core comprising a mixture of cellulosic pulp and superabsorbent polymer, where the core comprising the mixture defines:
    a single central zone comprising at least one insult area;
    a single continuous low-density zone surrounding the central zone, wherein the low-density zone is lower in density as compared to that of the central zone;
    a single continuous perimeter zone surrounding the low-density zone, wherein the perimeter zone is higher in density as compared to that of the low-density zone; and
    a single outboard zone surrounding the perimeter zone, wherein the outboard zone has the same density as the perimeter zone;
    wherein the thicknesses of the central zone, the low-density zone, and the perimeter zone are the same; and
    wherein the outboard zone has a thickness that is less than the thickness of the central zone, low-density zone and perimeter zone.

* * * * *